(12) United States Patent
Mou et al.

(10) Patent No.: US 10,928,370 B2
(45) Date of Patent: *Feb. 23, 2021

(54) ACTUATING AND SENSING MODULE

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Chang-Yen Tsai, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 198 days.

This patent is subject to a terminal disclaimer.

(21) Appl. No.: 16/263,420

(22) Filed: Jan. 31, 2019

(65) Prior Publication Data
US 2019/0302073 A1 Oct. 3, 2019

(30) Foreign Application Priority Data
Mar. 30, 2018 (TW) .................. 107111386

(51) Int. Cl.
*G01N 33/00* (2006.01)
*G01N 33/497* (2006.01)
(Continued)

(52) U.S. Cl.
CPC ....... *G01N 33/0027* (2013.01); *F04B 43/046* (2013.01); *G01N 33/0022* (2013.01);
(Continued)

(58) Field of Classification Search
CPC .......... G01N 33/0027; G01N 33/0022; G01N 33/0031; G01N 33/497; H04M 1/035; F04B 43/046
(Continued)

(56) References Cited

U.S. PATENT DOCUMENTS 10,677,773 B2 * 6/2020 Mou .................... G01N 33/004
2014/0134053 A1 5/2014 Mayer et al.

FOREIGN PATENT DOCUMENTS

CN 205538890 U 8/2016
CN 103975231 B 7/2017
(Continued)

*Primary Examiner* — Tarun Sinha
(74) *Attorney, Agent, or Firm* — Birch, Stewart, Kolasch & Birch, LLP

(57) ABSTRACT

An actuating and sensing module includes a main body, an actuator and a gas sensor. The main body includes a partition, an inlet and an outlet. The space inside the main body is divided into a first compartment and a second compartment by the partition. The inlet and the outlet are in fluid communication with the first compartment and the second compartment respectively. The inlet, the first compartment, a communicating hole, the second compartment and the outlet form a gas channel within the main body. The actuator is sealed and disposed between the main body and the partition in the second compartment, wherein gas is introduced into the first compartment through the inlet, transported to the second compartment through the communicating hole, and discharged through the outlet by the actuator. The gas sensor is disposed in the first compartment and separated from the actuator for monitoring the gas on a surface thereof.

14 Claims, 11 Drawing Sheets

(51) Int. Cl.
  *H01L 41/053*  (2006.01)
  *H05K 1/18*   (2006.01)
  *H04M 1/03*   (2006.01)
  *F04B 43/04*  (2006.01)

(52) U.S. Cl.
  CPC ....... *G01N 33/0031* (2013.01); *G01N 33/497* (2013.01); *H01L 41/053* (2013.01); *H04M 1/035* (2013.01); *H05K 1/181* (2013.01); *H05K 2201/10151* (2013.01)

(58) Field of Classification Search
  USPC ........................................................ 73/31.05
  See application file for complete search history.

(56) References Cited

FOREIGN PATENT DOCUMENTS

| | | |
|---|---|---|
| EP | 2905673 A2 | 8/2015 |
| EP | 2998582 A1 | 3/2016 |
| EP | 3203079 A1 | 8/2017 |
| TW | M553862 U | 1/2018 |
| TW | I618922 B | 3/2018 |

\* cited by examiner

ACTUATING AND SENSING MODULE

FIELD OF THE INVENTION

The present disclosure relates to an actuating and sensing module, and more particularly to an actuating and sensing module assembled in a thin portable device for monitoring ambient gas.

BACKGROUND OF THE INVENTION

Nowadays, people pay much attention to the air quality in the environment. For example, it is important to monitor carbon monoxide, carbon dioxide, volatile organic compounds (VOC), Particulate Matter 2.5 (PM2.5), nitric oxide, sulfur monoxide, and so on. The exposure of these substances in the environment will cause human health problems or even threaten the human life. Therefore, it is important for every country to improve the air quality.

Generally, it is feasible to use a gas sensor to monitor the air quality in the environment. If the gas sensor is capable of immediately providing people with the monitored information relating to the environment for caution, it may help people escape or prevent from the injuries and influence on human health caused by the exposure of the substances described above in the environment. In other words, the gas sensor is suitably used for monitoring the ambient gas in the environment.

Nowadays, the gas sensor monitors the environmental gas transported to the surface of the gas sensor. If there is no actuator for guiding the gas and increasing the flow rate of the gas, the time of the gas flowing to the gas sensor may be too long, which reduces the efficiency of sensing. However, if the actuator is provided to form an actuating and sensing module, the heat is generated due to continuous vibration of the actuator at high speed during operation. The generated heat is transferred to the surrounding of the gas sensor constantly. Therefore, the heat makes the gas to be sensed around the gas sensor different from the gas around the actuating and sensing module, and the monitoring result of the gas sensor is affected. In addition, when the actuating and sensing module is applied on and assembled with a device (e.g., portable electronic device), some interfering substances (e.g., gas pollution and heat) may be generated inside the device during the operation of the electronic elements (e.g., circuit board and processor) within the device. When the interfering substances are guided into the actuating and sensing module or mixed with the gas to be sensed, the monitoring quality of the gas sensor is affected. Namely, the actual characteristics and components of the gas to be sensed around the actuating and sensing module cannot be obtained, which means the sensing result is inaccurate.

Therefore, there is a need of providing an actuating and sensing module for increasing the efficiency of sensing, monitoring the gas to be sensed certainly, and decreasing the effect of the extrinsic factor on the gas sensor.

SUMMARY OF THE INVENTION

An object of the present disclosure provides an actuating and sensing module capable of being assembled in a thin portable device for monitoring ambient gas. The actuating and sensing module includes a main body, an actuator and a gas sensor. The disposition of the actuator increases the speed of transporting gas to the surface of the gas sensor for monitoring, and thus the sensing efficiency of the gas sensor is enhanced. Moreover, the main body has a monitoring chamber with one-way opening for introducing or discharging the gas in single direction. More specifically, the monitoring chamber has two openings, one for inhaling the air and the other one for discharging the air. The air inhaled in the monitoring chamber does not flow back along the same path to be discharged from the same opening. The actuator drives the resonance plate to transport the gas. Therefore, the gas outside the thin portable device is guided thereinto by the actuating and sensing module for monitoring. The characteristic of the gas to be monitored within the actuating and sensing module is the same as the characteristic of the gas outside the thin portable device.

In accordance with an aspect of the present disclosure, an actuating and sensing module is provided. The actuating and sensing module includes a main body, an actuator and a gas sensor. The main body includes a partition, an inlet and an outlet. The space inside the main body is divided into a first compartment and a second compartment by the partition. The inlet is in fluid communication with the first compartment. The outlet is in fluid communication with the second compartment. The partition has a communicating hole, and the first compartment and the second compartment are in fluid communication with each other through the communicating hole. The inlet, the first compartment, the communicating hole, the second compartment and the outlet form a gas channel within the main body. The actuator is sealed and disposed between the main body and the partition in the second compartment, wherein gas is introduced into the first compartment through the inlet, transported to the second compartment through the communicating hole, and discharged through the outlet by the actuator, by which an one-way gas transportation in the gas channel is formed. The gas sensor is disposed in the first compartment and separated from the actuator, wherein the gas sensor is configured for monitoring the gas on a surface of the gas sensor.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
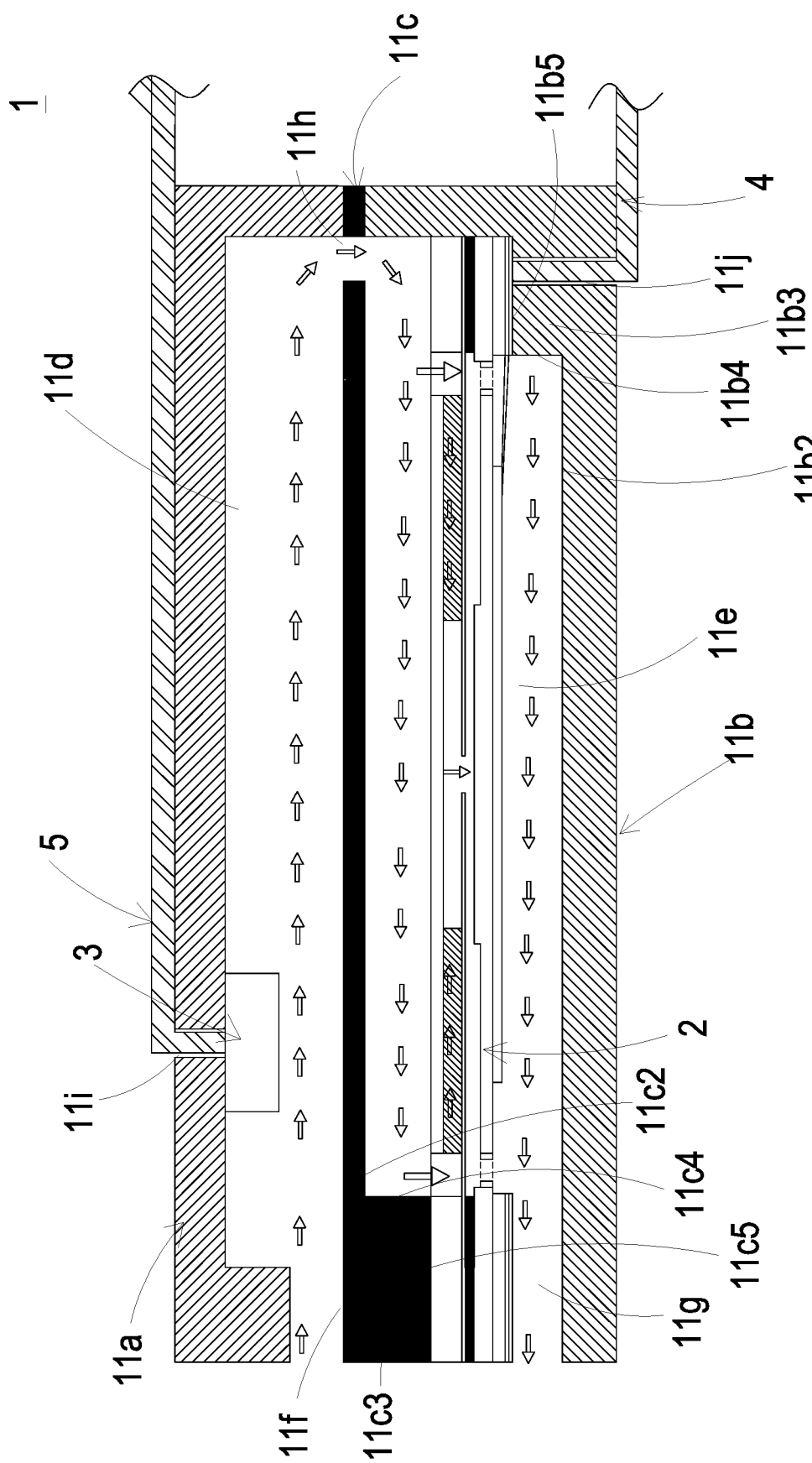
FIG. 1 is a schematic cross-sectional view illustrating an actuating and sensing module according to an embodiment of the present disclosure.

Please refer to FIG. 1. The present discourse provides an actuating and sensing module including at least one main body 1, at least one actuator 2, at least one gas sensor 3, at least one partition 11c, at least one first compartment 11d, at least one second compartment 11e, at least one inlet 11f, at least one outlet 11g, at least one communicating hole 11h, and at least one gas channel. The number of the main body 1, the actuator 2, the gas sensor 3, the partition 11c, the first compartment 11d, the second compartment 11e, the inlet 11f, the outlet 11g, the communicating hole 11h, and the gas channel is exemplified by one for each in the following embodiments but not limited thereto. It is noted that each of the main body 1, the actuator 2, the gas sensor 3, the partition 11c, the first compartment 11d, the second compartment 11e, the inlet 11f, the outlet 11g, the communicating hole 11h, and the gas channel can also be provided in plural numbers.

The present disclosure provides an actuating and sensing module. Please refer to FIGS. 1 to 3. The actuating and sensing module includes a main body 1, an actuator 2 and a gas sensor 3. The main body 1 includes a first body 11a, a second body 11b and a partition 11c. The first body 11a and the second body 11b are assembled with each other. The partition 11c is disposed between the first body 11a and the second body 11b so that the first body 11a, the second body 11b and the partition 11c in combination form the main body 1. Thus, the interior space enclosed by the main body 1 is divided into a first compartment 11d and a second compartment 11e by the partition 11c. An inlet 11f is disposed between the first body 11a and the partition 11c and is in fluid communication with the first compartment 11d. An outlet 11g is disposed between the second body 11b and the partition 11c and is in fluid communication with the second compartment 11e. Both of the inlet 11f and the outlet 11g are disposed on the same side of the main body 1. In addition, the partition 11c has a communicating hole 11h, and the first compartment 11d and the second compartment 11e are in fluid communication with each other through the communicating hole 11h. The inlet 11f, the first compartment 11d, the communicating hole 11h, the second compartment 11e and the outlet 11g form a gas channel within the main body 1 for transporting and discharging the gas in one-way (the path illustrated by the arrows in FIG. 1). Rather than being inhaled and discharged by the same opening, the air is inhaled from the inlet 11f, flows along the gas channel, and then is discharged through the outlet 11g into the environment outside the main body 1.

The actuator 2 is sealed and disposed between the second body 11b and the partition 11c. In this embodiment, the actuator 2 is disposed within the second compartment 11e. One end of the actuator 2 is securely mounted on the second body 11b, the other end of the actuator 2 is securely mounted on the partition 11c, and thus the second compartment 11e is sealed, which will be described in more detail below. The partition 11c has an inner surface 11c2 and a protrusion portion 11c3 protruding from the inner surface 11c2. The protrusion portion 11c3 has a top surface 11c5 and a sidewall 11c4 extending from the inner surface 11c2 to connect to the top surface 11c5. The second body 11b has an inner surface 11b2 and a protrusion portion 11b3 protruding from the inner surface 11b2. The protrusion portion 11b3 has a top surface 11b5 and a sidewall 11b4 extending from the inner surface 11b2 to connect to the top surface 11b5. One end of the actuator 2 attaches to the top surface 11c5, and seals the edge of the sidewall 11c4 of the protrusion portion 11c3. The other end of the actuator 2 attaches to the top surface 11b5, and seals the edge of the sidewall 11b4 of the protrusion portion 11b3. In other words, the protrusion portion 11c3 and the protrusion portion 11b3 extends in opposite directions, thereby providing two platforms for supporting the actuator 2. Also, the design of the protrusion portion 11c3 allows one part of the gas channel in the second compartment 11e to be formed between the actuator 2 and the partition 11c, and the design of the protrusion portion 11b3 allows another part of the gas channel in the second compartment 11e to be formed between the actuator 2 and the second body 11b. The actuator 2 is actuated to transport the gas, so that a negative pressure is formed in the second compartment 11e. The negative pressure allows the gas to be inhaled through the inlet 11f to the first compartment 11d, and the gas flows to the second compartment 11e through the communicating hole 11h. As the actuator 2 is continuously actuated to transport the gas, the gas in the second compartment 11e is pushed and discharged from the outlet 11g into the environment outside the main body 1. Consequently, the one-way gas transportation is realized.

The gas sensor 3 is disposed in the first compartment 11d and is separated from the actuator 2. The gas sensor 3 is configured for monitoring the gas flowing on a surface thereof. The gas sensor 3 and the actuator 2 are separated from each other by the partition 11c. That is, the partition 11c divides the space, enclosed by the main body 1, into two compartments. The gas sensor 3 is disposed in the first compartment 11d and the actuator 2 is disposed in the second compartment 11e, by which the gas sensor 3 is spatially separated from the actuator 2. When the actuator 2 is actuated to transport the gas, the heat is generated due to the continuous vibration of the actuator 2 at high speed during operation. Under this circumstance, the partition 11c may function as a barrier (e.g., a thermal insulation plate), and suppress the interference caused by the generated heat. The partition 11c prevents the generated heat from interfering with the gas sensor 3.

In this embodiment, the gas sensor 3 may include at least one selected from the group consisting of an oxygen sensor, a carbon monoxide sensor, a carbon dioxide sensor, a temperature sensor, an ozone sensor, a volatile organic compound (VOC) sensor and combinations thereof. Alternatively, the gas sensor 3 may include at least one selected from a group consisting of a bacterial sensor, a virus sensor, a microorganism sensor and combinations thereof.

Please refer to FIG. 1. The first body 11a of the actuating and sensing module has a first connecting perforation 11i. The first connecting perforation 11i is configured for a flexible circuit board 5 to penetrate therethrough and connect to the gas sensor 3. After connecting the flexible circuit board 5 to the gas sensor 3, the first connecting perforation 11i is sealed by a potting compound to prevent the gas from flowing into the first compartment 11d therethrough. The second body 11*b* of the actuating and sensing module has a second connecting perforation 11*j*. The second connecting perforation 11*j* is configured for a flexible circuit board 5 to penetrate therethrough and connect to the actuator 2. After connecting the flexible circuit board 5 to the actuator 2, the second connecting perforation 11*j* is sealed by a potting compound to prevent the gas from flowing into the second compartment 11*e* therethrough. Consequently, the actuating and sensing module acts as a monitoring chamber with one-way opening, and the one-way gas transportation and the gas monitoring are realized.

Figure 2:
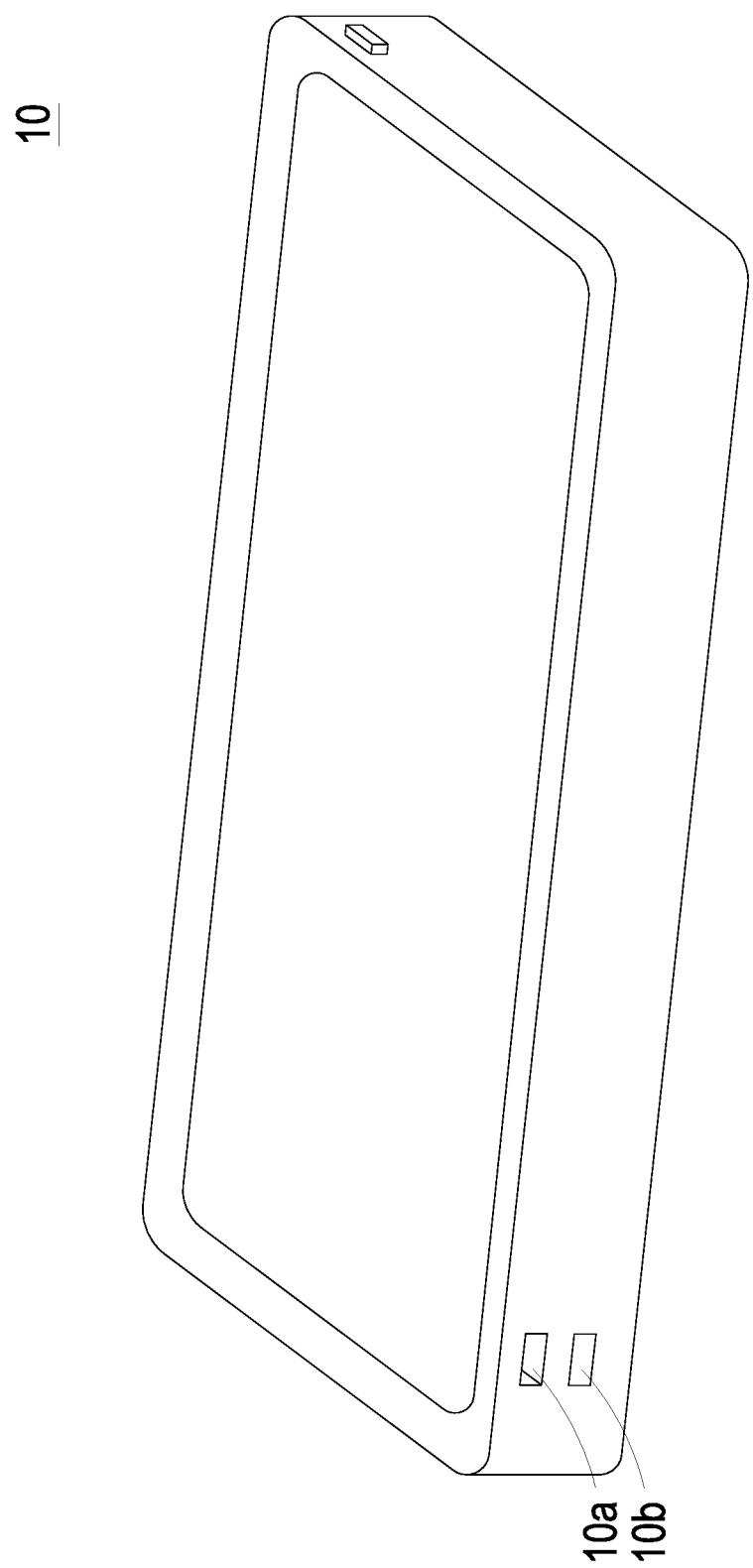
FIG. 2 is a schematic view showing the actuating and sensing module applied in a thin portable device according to an embodiment of the present disclosure.
Figure 3:
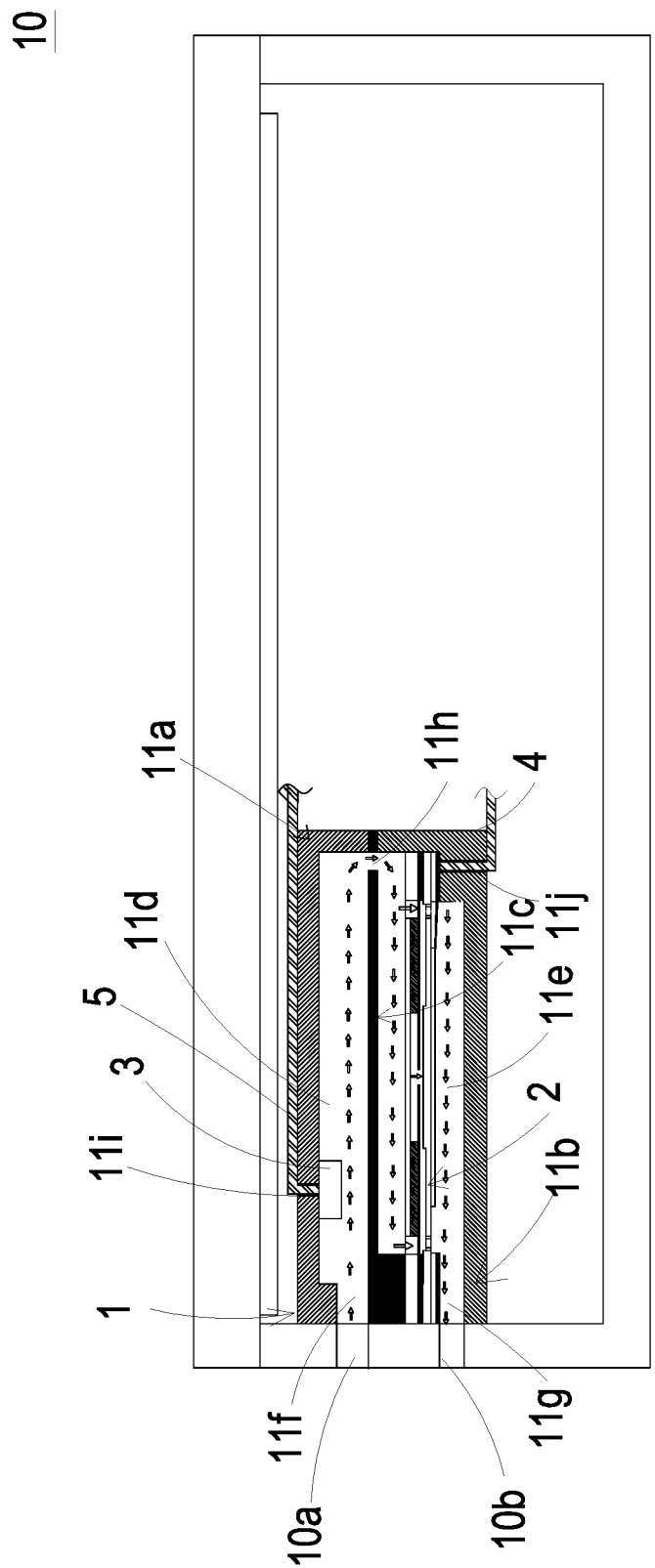
FIG. 3 is a schematic cross-sectional view illustrating the actuating and sensing module applied in the thin portable device of FIG. 2.
Figure 4A:
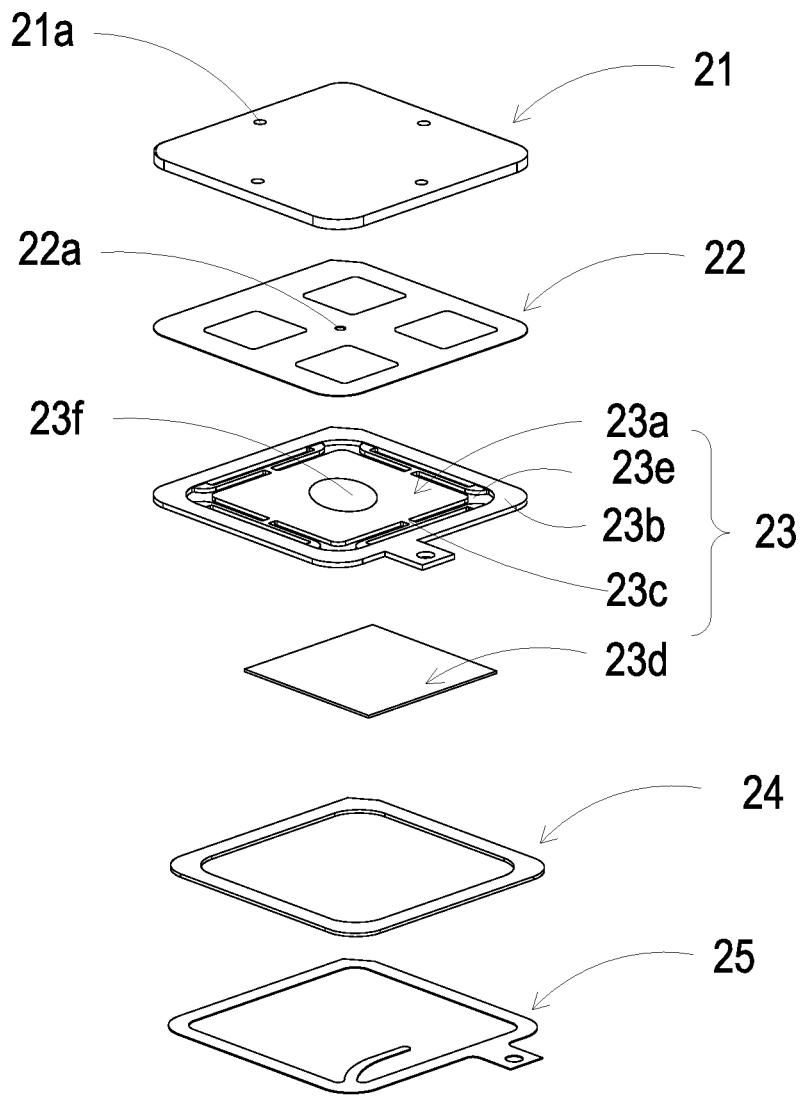
FIG. 4A is a schematic exploded view illustrating an actuator of the actuating and sensing module of the present disclosure.
Figure 4B:
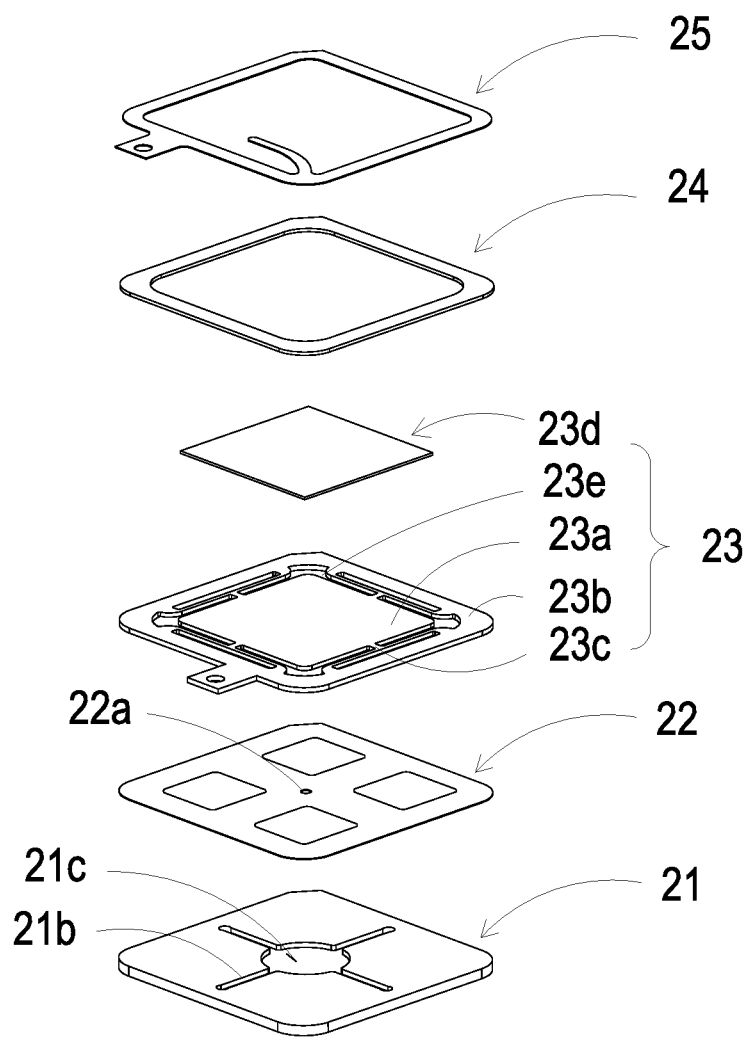
FIG. 4B is a schematic exploded view illustrating the actuator of the actuating and sensing module of the present disclosure and taken along another viewpoint.

Please refer to FIGS. 2 and 3. The actuating and sensing module can be applied and assembled in a thin portable device 10. The thin portable device 10 includes a first opening 10*a* and a second opening 10*b*. The first opening 10*a* and the second opening 10*b* are opened on the same sidewall of the thin portable device 10. The actuating and sensing module is assembled within the thin portable device 10. The inlet 11*f* and the outlet 11*g* of the actuating and sensing module are corresponding in position to the first opening 10*a* and the second opening 10*b* respectively. Thus, the gas outside the thin portable device 10 can be guided into the thin portable device 10 for monitoring, and after monitoring the gas, the gas flows from the first compartment 11*d* into the second compartment 11*e* and then is discharged into the environment outside the main body 1. More specifically, as the actuator 2 is actuated, the negative pressure is formed in the first compartment 11*d*. The negative pressure allows the gas to be inhaled through the inlet 11*f* to the first compartment 11*d*, and the gas flows to the second compartment 11*e* through the communicating hole 11*h*. The actuator 2 is actuated to transport the gas, so that the gas within the second compartment 11*e* is pushed and discharged from the outlet 11*g*. Consequently, the one-way gas transportation and the gas monitoring are realized. The actuating and sensing module of the present disclosure isolates the interfering factors (the interfering substances such as the heat generated by the internal actuators and the heat and gas pollution generated within the thin portable device 10) from affecting the gas sensor 3. Besides, the actuator 2, which is disposed for inhaling and discharging the gas, enhances the rate of transporting the gas to the surface of the gas sensor 3 for monitoring. The sensing efficiency of the gas sensor is increased due to the design of the actuator 2. The present disclosure achieves the purpose of monitoring the gas that can reflect the actual condition in the environment. The characteristic of the gas to be monitored in the actuating and sensing module is the same as the characteristic of the gas outside the thin portable device 10.

After the descriptions about the characteristic of the actuating and sensing module, the structure and action of the actuator 2 are described as follows.

Please refer to FIGS. 4A to 5A. In an embodiment, the actuator 2 is a gas pump. The actuator 2 includes a gas inlet plate 21, a resonance plate 22, a piezoelectric actuator 23, an insulation plate 24 and a conducting plate 25, which are stacked on each other sequentially. The gas inlet plate 21 has at least one inlet aperture 21*a*, at least one convergence channel 21*b* and a convergence chamber 21*c*. The number of the inlet aperture 21*a* is the same as the number of the convergence channel 21*b*. In this embodiment, the number of the inlet aperture 21*a* and the convergence channel 21*b* is exemplified by four for each but not limited thereto. The four inlet apertures 21*a* penetrate through the four convergence channels 21*b* respectively, and the four convergence channels 21*b* converge to the convergence chamber 21*c*.

The resonance plate 22 is assembled on the gas inlet plate 21 by attaching. The resonance plate 22 has a central aperture 22*a*, a movable part 22*b* and a fixed part 22*c*. The central aperture 22*a* is located at the center of the resonance plate 22 and is aligned with the convergence chamber 21*c* of the gas inlet plate 21. The region of the resonance plate 22 around the central aperture 22*a* and corresponding to the convergence chamber 21*c* is the movable part 22*b*. The region of the periphery of the resonance plate 22 securely attached on the gas inlet plate 21 is the fixed part 22*c*.

The piezoelectric actuator 23 includes a suspension plate 23*a*, an outer frame 23*b*, at least one connecting part 23*c*, a piezoelectric element 23*d*, at least one vacant space 23*e* and a bulge 23*f*. The suspension plate 23*a* is a square suspension plate and has a first surface 231*a* and a second surface 232*a* opposite to the first surface 231*a*. The outer frame 23*b* is disposed around the periphery of the suspension plate 23*a*. The outer frame 23*b* has an assembling surface 231*b* and a bottom surface 232*b* opposite to the assembling surface 231*b*. The at least one connecting part 23*c* is connected between the suspension plate 23*a* and the outer frame 23*b* for elastically supporting the suspension plate 23*a*. The at least one vacant space 23*e* is formed among the suspension plate 23*a*, the outer frame 23*b* and the at least one connecting part 23*c* for allowing the gas to flow through.

In addition, the first surface 231*a* of the suspension plate 23*a* has the bulge 23*f*. In this embodiment, the formation of the bulge 23*f* may be completed by using an etching process, in which the region between the periphery of the bulge 23*f* and the junction at the connecting part 23*c* is partially removed. Accordingly, the bulge 23*f* of the suspension plate 23*a* is higher than the first surface 231*a*, and a stepped structure is formed.

Figure 5A:
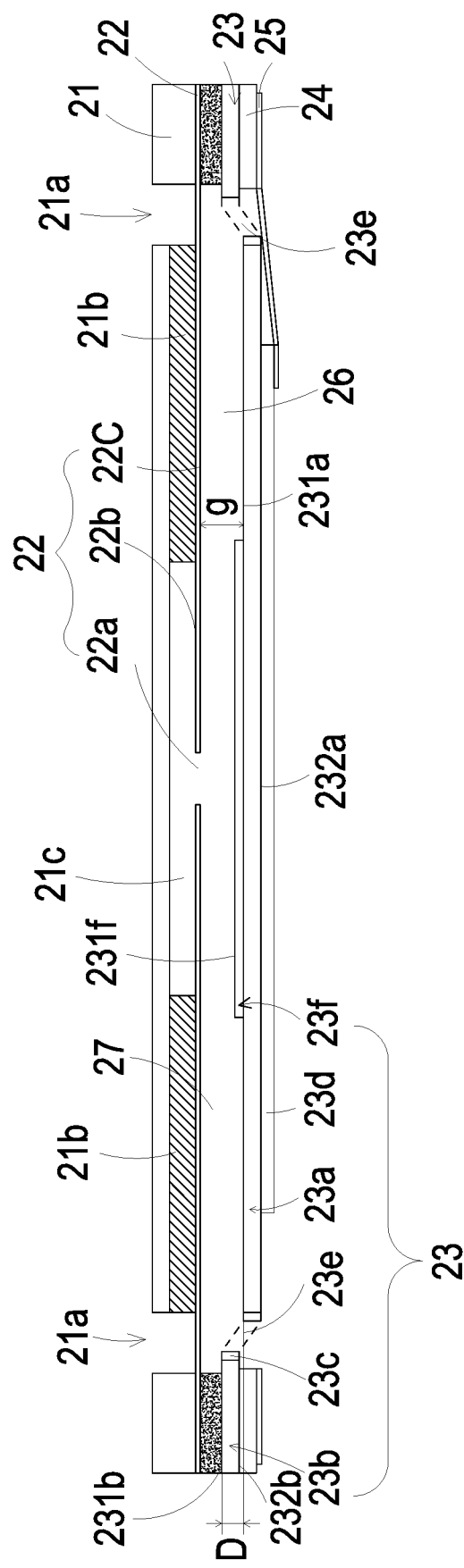
FIG. 5A is a schematic cross-sectional view illustrating the actuator of the actuating and sensing module of the present disclosure.

As shown in FIG. 5A, in this embodiment, the suspension plate 23*a* may be further processed by using a stamping method, by which the outer frame 23*b*, the at least one connecting part 23*c*, and the suspension plate 23*a* have a concave profile in cross section. The stamping method makes the suspension plate 23*a* away from the resonance plate 22*a* distance D, which can be adjusted by the at least one connecting part 23*c* formed between the suspension plate 23*a* and the outer frame 23*b*. Consequently, the top surface 231*f* of the bulge 23*f* and the first surface 231*a* of the suspension plate 23*a* are not coplanar with the assembling surface 231*b* of the outer frame 23*b*. Namely, the top surface 231*f* of the bulge 23*f* and the first surface 231*a* of the suspension plate 23*a* are lower than the assembling surface 231*b* of the outer frame 23*b*, and the second surface 232*a* of the suspension plate 23*a* is lower than the bottom surface 232*b* of the outer frame 23*b*. In the embodiment, the piezoelectric element 23*d* is attached on the second surface 232*a* of the suspension plate 23*a* and is disposed opposite to the bulge 23*f*. A length of a side of the piezoelectric element 23*d* is smaller than or equal to a length of a side of the suspension plate 23*a*. In response to an applied driving voltage, the piezoelectric element 23*d* is subjected to a deformation owing to the piezoelectric effect so as to drive the suspension plate 23*a* to bend and vibrate. In an embodiment, a small amount of adhesive is applied to the assembling surface 231*b* of the outer frame 23*b*, and the piezoelectric actuator 23 is attached on the fixed part 22*c* of the resonance plate 22 after a hot pressing process. Therefore, the piezoelectric actuator 23 and the resonance plate 22 are assembled together.

In addition, the insulation plate 24 and the conducting plate 25 are both thin frame-shaped plate, which are stacked sequentially under the piezoelectric actuator 23. In this embodiment, the insulation plate 24 is attached on the bottom surface 232b of the outer frame 23b of the piezoelectric actuator 23.

Please refer to FIG. 5A. The gas inlet plate 21, the resonance plate 22, the piezoelectric actuator 23, the insulation plate 24 and the conducting plate 25 of the actuator 2 are stacked on each other sequentially. A chamber gap g is formed between the first surface 231a of the suspension plate 23a and the resonance plate 22. Since the distance between the suspension plate 23a and the resonance plate 22 will influence the transportation efficiency of the actuator 2, it is important to maintain the chamber gap g for providing a stable transportation efficiency of the actuator 2. The suspension plate 23a of the actuator 2 is processed by the stamping method as described above, and it makes the suspension plate 23a disposed further away from the resonance plate 22. Consequently, the first surface 231a of the suspension plate 23a and the top surface 231f of the bulge 23f are not coplanar with the assembling surface 231b of the outer frame 23b. Namely, the first surface 231a of the suspension plate 23a and the top surface 231f of the bulge 23f are lower than the assembling surface 231b of the outer frame 23b, and the second surface 232a of the suspension plate 23a is lower than the bottom surface 232b of the outer frame 23b. In this way, the entire structure may be improved by adopting the stamping method to process the suspension plate 23a. The space between the suspension plate 23a of the piezoelectric actuator 23 and the resonance plate 22 is adjustable due to the stamping method, by which the adjustable chamber gap g is realized. That is, the design of a chamber space 26 is improved by processing the suspension plate 23a of the piezoelectric actuator 23 to be disposed further away from the resonance plate 22. The desired chamber gap g can be satisfied by simply adjusting the distance D, as described above. It simplifies the structural design regarding the adjustment of the chamber gap g, and it also achieves the advantages of simplifying the process and shortening the processing time.

Figure 5B:
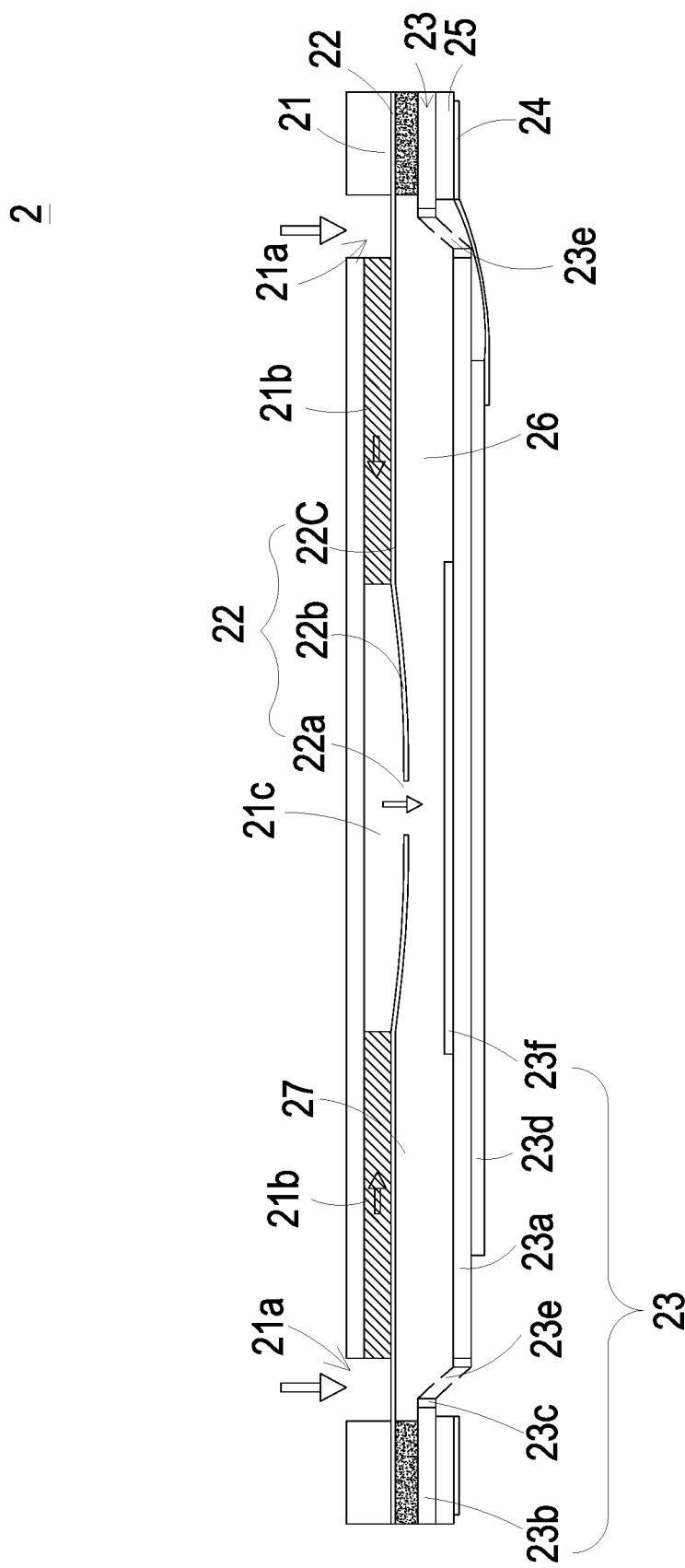
FIGS. 5B to 5D schematically illustrate the actions of the actuator of the actuating and sensing module of the present disclosure.
Figure 5C:
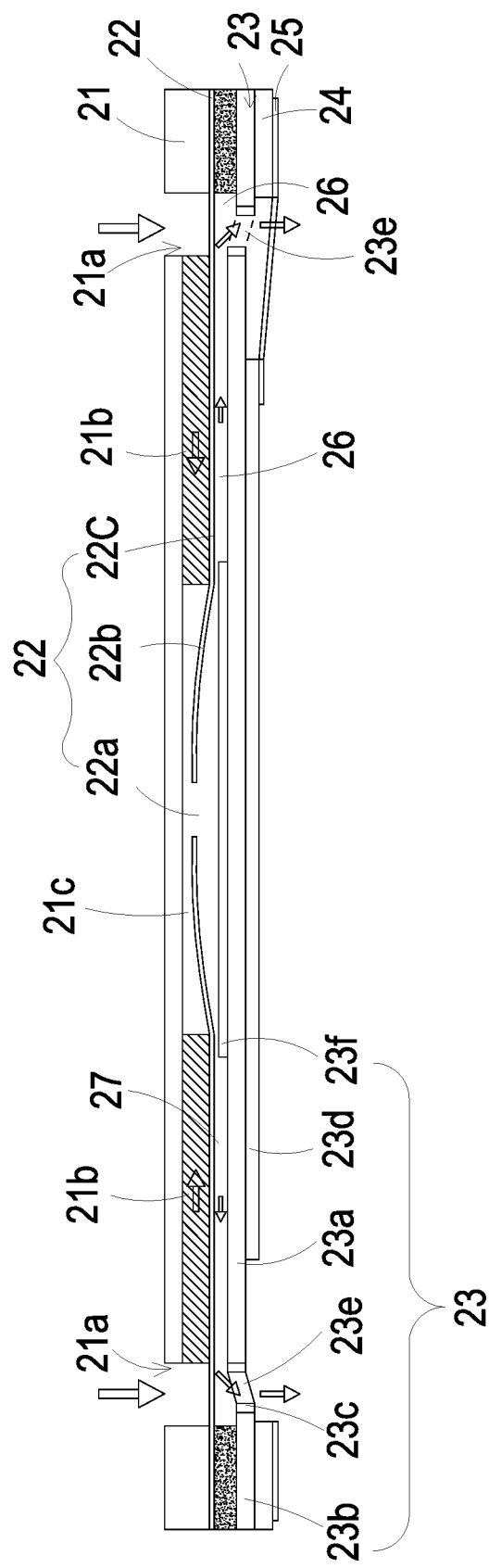
Figure 5D:
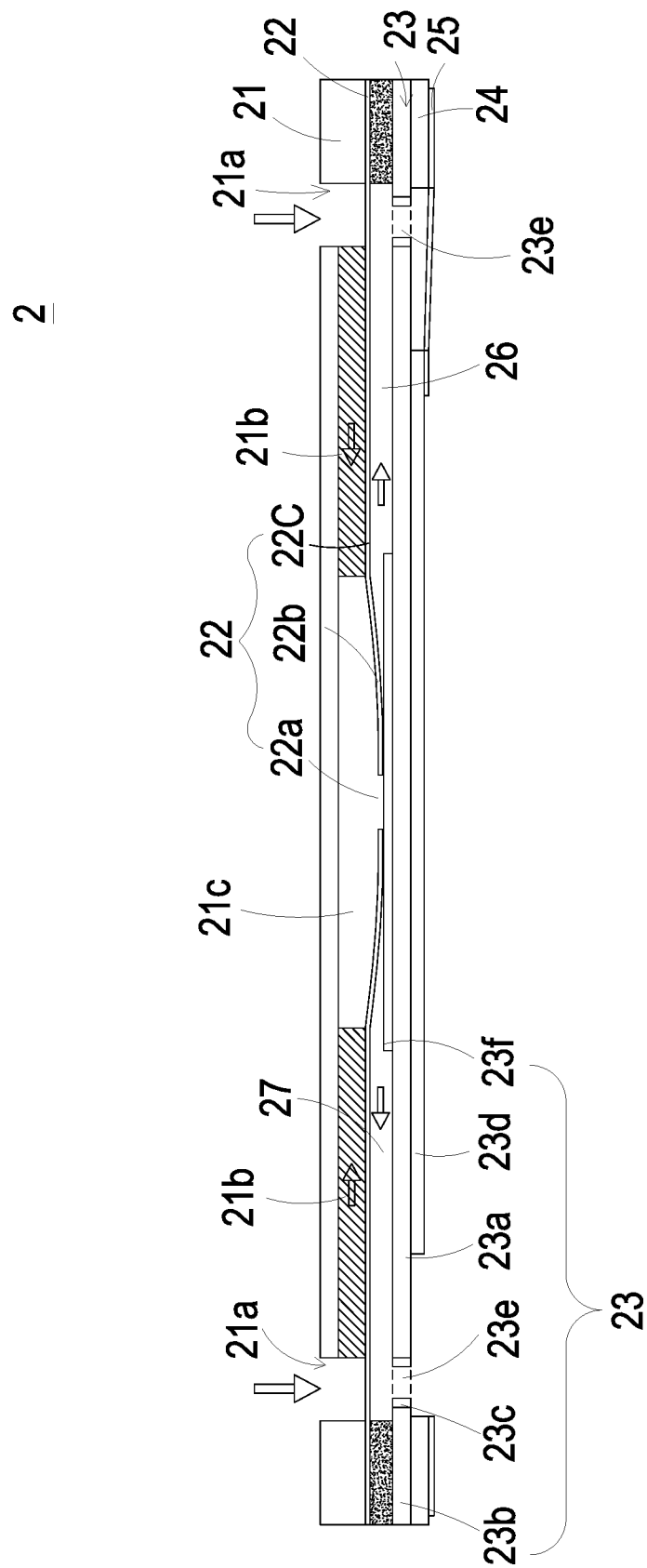

FIGS. 5B to 5D schematically illustrate the actions of the actuator 2 of FIG. 5A. Please refer to FIG. 5B. When a driving voltage is applied to the piezoelectric element 23d of the piezoelectric actuator 23, the piezoelectric element 23d deforms to drive the suspension plate 23a to move in the direction away from the gas inlet plate 21. Meanwhile, the volume of the chamber space 26 is increased, and a negative pressure is formed in the chamber space 26 so that the air in the convergence chamber 21c is inhaled into the chamber space 26. At the same time, the resonance plate 22 is in resonance with the piezoelectric actuator 23 to move in the direction away from the gas inlet plate 21, so that the volume of the convergence chamber 21c is expanded. Since the air in the convergence chamber 21c is transported to the chamber space 26, a negative pressure is formed in the convergence chamber 21c. The negative pressure allows the air to be inhaled through the convergence channel 21b and the inlet aperture 21a to the convergence chamber 21c. Please refer to FIG. 5C. The piezoelectric element 23d drives the suspension plate 23a to move toward the gas inlet plate 21, and the volume of the chamber space 26 is compressed, so that the air in the chamber space 26 is forced to flow through the vacant space 23e in the direction away from the gas inlet plate 21. Thereby, the air transportation efficacy is achieved. Meanwhile, the resonance plate 22 is moved toward the gas inlet plate 21 in resonance with the suspension plate 23a, and the air in the convergence chamber 21c is pushed to move toward the chamber space 26 synchronously. Please refer to FIG. 5D. When the suspension plate 23a is driven to move in the direction away from the gas inlet plate 21, the resonance plate 22 is moved in the direction away from the gas inlet plate 21 in resonance with the suspension plate 23a. Meanwhile, the air in the chamber space 26 is compressed by the resonance plate 22 and is transferred toward the vacant space 23e. The volume of the convergence chamber 21c is expanded, and the air is allowed to flow through the inlet aperture 21a and the convergence channel 21b and converge in the convergence chamber 21c continuously. By repeating the above steps, the air is continuously introduced through the inlet aperture 21a into the actuator 2, and then the air is transferred through the vacant space 23e in the direction away from the gas inlet plate 21. Consequently, the efficacy of transferring the air to the gas sensor 3 is achieved. The air is continuously provided to the gas sensor 3 for detection, thus the efficiency of detecting is increased.

Please refer to FIG. 5A. In another embodiment, by utilizing the micro-electro-mechanical technology, the actuator 2 is a micro-electro-mechanical-system (MEMS) gas pump. Preferably but not exclusively, the gas inlet plate 21, the resonance plate 22, the piezoelectric actuator 23, the insulation plate 24 and the conducting plate 25 are manufactured by surface micromachining to reduce the volume of the actuator 2.

Figure 6:
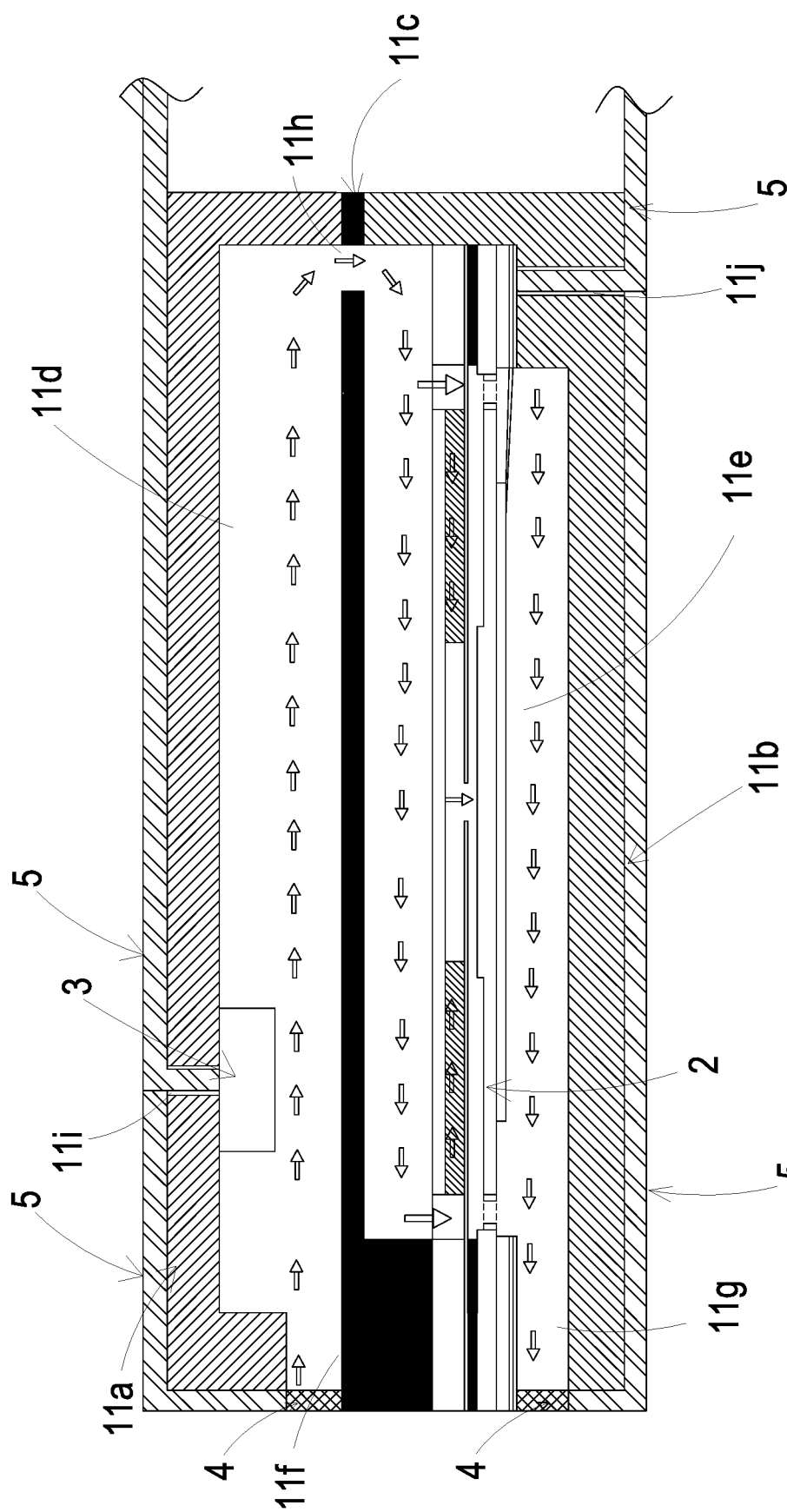
FIG. 6 is a schematic view showing the actuating and sensing module applied in a thin portable device according to another embodiment of the present invention.

Please refer to FIG. 6. In some embodiments, the actuating and sensing module further includes at least one valve 4. In this embodiment, the number of the valve 4 is two, and the two valves 4 are disposed at the inlet 11f and the outlet 11g respectively. The valves 4 are configured for opening and closing the inlet 11f and the outlet 11g. The valves 4 seal the inlet 11f and the outlet 11g. As the valves 4 are in the closed state, the interior space enclosed by the main body 1 is completely isolated from the environment outside the main body 1, and vise versa. For example, in particular, since the boiling point of the volatile organic compound is relatively low and is easily affected by environmental factors, the valves 4 are utilized to close the inlet 11f and the outlet 11g during sensing the volatile organic compound. By the first body 11a and the second body 11b, the external factors are prevented from affecting the interior of the actuating and sensing module. Moreover, the actuator 2 is spatially separated from the gas sensor 3 by the partition 11c, and it prevents the generated heat of the actuator 2 from interfering with the gas sensor 3. Thus, the gas sensor 3 can sense the quantity of the volatile organic compound actually contained in the air in the actuating and sensing module without being affected by environmental factors.

Figure 7A:
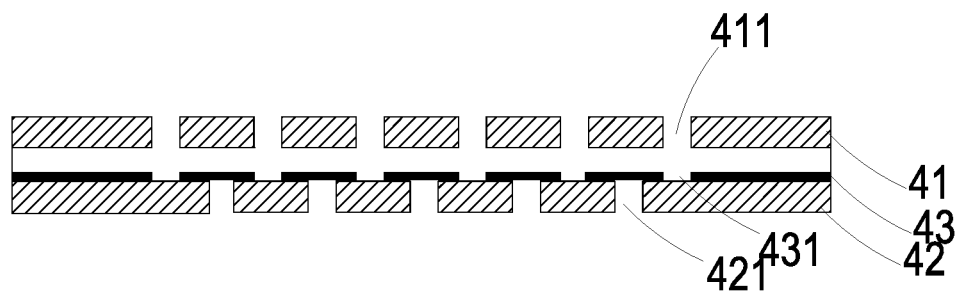
FIG. 7A is a schematic view illustrating a valve of the actuating and sensing module of FIG. 6.
Figure 7B:
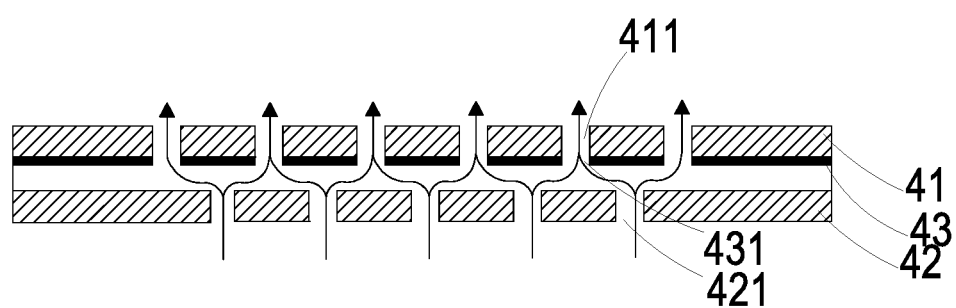
FIG. 7B schematically illustrates the actions of the valve of the actuating and sensing module of FIG. 7A.

Please refer to FIG. 7A and FIG. 7B. The valve 4 includes a stationary component 41, a sealing component 42 and a displacement component 43. The displacement component 43 is disposed and displaced between the stationary component 41 and the sealing component 42. The stationary component 41 has a plurality of first orifices 411. The sealing component 42 has a plurality of second orifices 421. The displacement component 43 has a plurality of third orifices 431 corresponding in position to the plurality of first orifices 411 of the stationary component 41 respectively. That is, the plurality of first orifices 411 of the stationary component 41 are aligned with the plurality of third orifices 431 of the displacement component 43. The plurality of second orifices 421 of the sealing component 42 are misaligned with the plurality of first orifices 411 of the stationary component 41. The stationary component 41, the sealing component 42 and the displacement component 43 of the valve 4 are controlled via a processor (not shown) connected to the flexible circuit board 5 so as to control the displacement component 43 to move toward the stationary component 41 and make the valve 4 in an open state.

In a first aspect of the valve 4 in the present disclosure, the displacement component 43 is made of a charged material, and the stationary component 41 is made of a bipolar conductive material. The stationary component 41 is controlled by the processor electrically connected with the flexible circuit board 5 so as to control the polarity (positive electrical polarity or the negative electrical polarity) of the stationary component 41. In the case that the displacement component 43 is made of a negatively charged material, and the valve 4 needs to be controlled to open, the stationary component 41 is controlled to form a positive electrode. In that, the displacement component 43 and the stationary component 41 are maintained in the opposite polarity, so that the displacement component 43 moves toward and attaches to the stationary component 41, and the valve 4 is in an open state (as shown in FIG. 7B). Alternatively, in case that the displacement component 43 is made of a negative-charged material, and the valve 4 needs to be controlled to close, the stationary component 41 is controlled to form a negative electrode. In that, the displacement component 43 and the stationary component 41 are maintained in the same polarity, so that the displacement component 43 moves toward and attaches to the sealing component 42, and the valve 4 is in a closed state (as shown in FIG. 7A).

In a second aspect of the valve 4 in the present disclosure, the displacement component 43 is made of a magnetic material, and the stationary component 41 is made of an electromagnet material and can be controlled to change its magnetic polarity. The stationary component 41 is controlled by the processor electrically connected with the flexible circuit board 5, so as to control the polarity (positive magnetic polarity or negative magnetic polarity) of the stationary component 41. In case that the displacement component 43 is made of a negative-magnetic material, and the valve 4 needs to be controlled to open, the stationary component 41 is controlled to form a positive-magnetic pole. In that, the displacement component 43 and the stationary component 41 are maintained in the opposite polarity, so that the displacement component 43 moves toward and attaches to the stationary component 41, and the valve 4 is in the open state (as shown in FIG. 7B). Alternatively, in case that the displacement component 43 is made of a negative-magnetic material, and the valve 4 needs to be controlled to close, the stationary component 41 is controlled to form a negative-magnetic pole. In that, the displacement component 43 and the stationary component 41 are maintained in the same polarity, so that the displacement component 43 moves toward and attaches to the sealing component 42, and the valve 4 is in the closed state (as shown in FIG. 7A).

From the above descriptions, the present disclosure provides an actuating and sensing module capable of being assembled in a thin portable device for monitoring ambient gas. The actuating and sensing module includes a main body, an actuator and a gas sensor. The disposition of the actuator increases the rate of transporting the gas to the surface of the gas sensor for monitoring, and thus the sensing efficiency of the gas sensor is enhanced. Moreover, the main body has a monitoring chamber with one-way opening for introducing or discharging the gas in single direction. The actuator drives the resonance plate to transport the gas. Therefore, the gas outside the thin portable device is guided thereinto by the actuating and sensing module for monitoring. The characteristic of the gas to be monitored within the actuating and sensing module is the same as the characteristic of the gas outside the thin portable device. The present disclosure is extremely valuable for industrial use.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An actuating and sensing module, comprising:
    a main body comprising a partition, an inlet and an outlet, wherein space inside the main body is divided into a first compartment and a second compartment by the partition, the inlet is in fluid communication with the first compartment, the outlet is in fluid communication with the second compartment, the partition has a communicating hole, and the first compartment and the second compartment are in fluid communication with each other through the communicating hole, wherein the inlet, the first compartment, the communicating hole, the second compartment and the outlet form a gas channel within the main body;
    an actuator sealed and disposed between the main body and the partition in the second compartment, wherein gas is introduced into the first compartment through the inlet, transported to the second compartment through the communicating hole, and discharged through the outlet by the actuator, whereby an one-way gas transportation in the gas channel is formed; and
    a gas sensor disposed in the first compartment and separated from the actuator, wherein the gas sensor is configured for monitoring the gas on a surface of the gas sensor.

2. The actuating and sensing module according to claim 1, wherein the gas sensor comprises at least one selected from the group consisting of an oxygen sensor, a carbon monoxide sensor, a carbon dioxide sensor and combinations thereof.

3. The actuating and sensing module according to claim 1, wherein the gas sensor comprises a volatile organic compound sensor.

4. The actuating and sensing module according to claim 1, wherein the gas sensor comprises at least one selected from the group consisting of a bacterium sensor, a virus sensor, a microorganism sensor and combinations thereof.

5. The actuating and sensing module according to claim 1, wherein the actuator is a micro-electromechanical-systems gas pump.

6. The actuating and sensing module according to claim 1, wherein the actuator is a gas pump, and the gas pump comprises:
    a gas inlet plate having at least one inlet aperture, at least one convergence channel and a convergence chamber, wherein the at least one inlet aperture allows the gas to flow in, and the at least one convergence channel is aligned with the at least one inlet aperture and guides the gas from the inlet aperture toward the convergence chamber;
    a resonance plate having a central aperture and a movable part, wherein the central aperture is aligned with the convergence chamber and the movable part surrounds the central aperture; and
    a piezoelectric actuator aligned with the resonance plate;

wherein the gas inlet plate, the resonance plate and the piezoelectric actuator are stacked sequentially, and a chamber space is formed between the resonance plate and the piezoelectric actuator, so that the gas from the at least one inlet aperture of the gas inlet plate is converged to the convergence chamber along the at least one convergence channel and flows into the chamber space through the central aperture of the resonance plate when the piezoelectric actuator is driven, whereby the gas is further transported through a resonance between the piezoelectric actuator and the movable part of the resonance plate.

7. The actuating and sensing module according to claim 6, wherein the piezoelectric actuator comprises:
   a suspension plate having a first surface and a second surface, wherein the suspension plate is permitted to under a bending vibration;
   an outer frame arranged around the suspension plate;
   at least one connecting part connected between the suspension plate and the outer frame for elastically supporting the suspension plate; and
   a piezoelectric element, wherein a length of a side of the piezoelectric element is smaller than or equal to a length of a side of the suspension plate, and the piezoelectric element is attached on the second surface of the suspension plate to drive the suspension plate to undergo the bending vibration in response to an applied voltage.

8. The actuating and sensing module according to claim 7, wherein the suspension plate is a square suspension plate and comprises a bulge disposed on the first surface of the suspension plate.

9. The actuating and sensing module according to claim 6, wherein the actuator comprises a conducting plate and an insulation plate, and the gas inlet plate, the resonance plate, the piezoelectric actuator, the insulation plate and the conducting plate are stacked sequentially.

10. The actuating and sensing module according to claim 1, wherein the main body comprises a first body and a second body, wherein the first body and the second body are assembled with each other, and the partition is disposed between the first body and the second body, so that the first compartment is formed between the first body and the partition, the second compartment is formed between the second body and the partition, the inlet is disposed between the first body and the partition and is in fluid communication with the first compartment, and the outlet is disposed between the second body and the partition and is in fluid communication with the second compartment.

11. The actuating and sensing module according to claim 10, wherein the first body has a first connecting perforation configured for a flexible circuit board to penetrate therethrough and connect to the gas sensor, and the first connecting perforation is sealed by a potting compound after connecting the flexible circuit board to the gas sensor, thereby preventing the gas from flowing into the first compartment therethrough.

12. The actuating and sensing module according to claim 10, wherein the second body has a second connecting perforation configured for a flexible circuit board to penetrate therethrough and connect to the actuator, and the second connecting perforation is sealed by a potting compound after connecting the flexible circuit board to the actuator, thereby preventing the gas from flowing into the second compartment therethrough.

13. The actuating and sensing module according to claim 1, wherein the actuating and sensing module further comprises at least one valve disposed at the inlet and the outlet respectively, wherein each valve comprises a stationary component, a sealing component and a displacement component, wherein the displacement component is disposed between the stationary component and the sealing component, the stationary component has a plurality of first orifices, the sealing component has a plurality of second orifices, and the displacement component has a plurality of third orifices, wherein the plurality of third orifices of the displacement component are aligned with the plurality of first orifices of the stationary component, and the plurality of second orifices of the sealing component are misaligned with the plurality of first orifices of the stationary component, wherein the displacement component is controlled via a processor connected to a flexible circuit board so as to control the displacement component to move toward the stationary component and make the valve in an open state.

14. An actuating and sensing module, comprising:
   at least one main body comprising at least one partition, at least one inlet and at least one outlet, wherein space inside the main body is divided into at least one first compartment and at least one second compartment by the partition, the inlet is in fluid communication with the first compartment, the outlet is in fluid communication with the second compartment, the partition has at least one communicating hole, and the first compartment and the second compartment are in fluid communication with each other through the communicating hole, wherein the inlet, the first compartment, the communicating hole, the second compartment and the outlet form at least one gas channel within the main body;
   at least one actuator sealed and disposed between the main body and the partition in the second compartment, wherein gas is introduced into the first compartment through the inlet, transported to the second compartment through the communicating hole, and discharged through the outlet by the actuator, whereby an one-way gas transportation in the gas channel is formed; and
   at least one gas sensor disposed in the first compartment and separated from the actuator, wherein the gas sensor is configured for monitoring the gas on a surface of the gas sensor.

\* \* \* \* \*